US005712113A

United States Patent [19]

Chung et al.

[11] Patent Number: 5,712,113
[45] Date of Patent: Jan. 27, 1998

[54] SIGNAL SEQUENCES FOR SECRETION OF HETEROLOGOUS PROTEINS FROM YEAST

[75] Inventors: Bong Hyun Chung; Soo Wan Nam, both of Daejeon; Byung Moon Kim, Chungju-si; Sun Ah Yang, Daegu; Young Hoon Park, Daejeon, all of Rep. of Korea

[73] Assignee: Korea Institute of Science and Technology, Seoul, Rep. of Korea

[21] Appl. No.: 353,751

[22] Filed: Dec. 12, 1994

[30] Foreign Application Priority Data

Dec. 10, 1993 [KR] Rep. of Korea ............ 1993-27269

[51] Int. Cl.$^6$ .................. C12P 21/06; C12N 1/19; C12N 15/81
[52] U.S. Cl. .................. 435/69.1; 435/254.21; 435/320.1
[58] Field of Search ............ 536/23.74; 435/320.1, 435/254.2, 254.21, 254.23, 69.9

[56] References Cited

U.S. PATENT DOCUMENTS

| | | | |
|---|---|---|---|
| 4,588,684 | 5/1986 | Brake et al. | 435/69.4 |
| 5,081,019 | 1/1992 | Wallner et al. | 435/69.2 |
| 5,432,082 | 7/1995 | Galeotti et al. | 435/252.33 |

FOREIGN PATENT DOCUMENTS 9105051  4/1991  WIPO .

OTHER PUBLICATIONS

Rouwenhorst, et al., *Appl. Environ. Microbiol.*, 56, pp. 3337–3345(1990).

Jung-Han Koh, *Studies on the Extracellular Secretion of Proteins in Yeast,* Doctoral thesis, Dept. of Agric. Chem., The University of Tokyo, 1990 (pp. 1–2).

George P. Livi, et al. "Secretion of N-glycosylated human recombinant interleukin-1 αin *Saccharomyces cerevisiae,* "Gene. 88 (1990) pp. 297–301.

Masao Tokunaga et al. "Expression of pGEL killer 28k subunit in *Saccharomyces cerevisiae* . . . " Laboratory of Molecular Genetics, Mitsubishi Kasei Institute of Life Sciences; Nucleic Acids Research, vol. 17(9), pp. 3435–3446 (1989).

Laloux et al, FEBS Letters, Sep. 1991, vol. 289 (1): pp. 64–68.

Emr et al, PNAS USA, Dec., 1983, vol. 80: pp. 7080–7084.

Bergkamp, R.J.M., et al., *Appl. Microbiol. Technol.*, 40, pp. 309–317 (1993).

*Primary Examiner*—George C. Elliott
*Assistant Examiner*—Terry A. McKelvey
*Attorney, Agent, or Firm*—Anderson Kill & Olick, P.C.

[57] ABSTRACT

Secretion signal peptides of inulinases derived from *Kluyveromyces marxianus*, which makes a heterologous protein produced in a yeast cell be secreted almost completely into the extracellular medium; nucleotide sequences encoding said secretion signal peptides; expression and secretion vectors comprising nucleotide sequences encoding said secretion signal peptides; recombinant yeast cells transformed with said expression and secretion vectors; and a process for producing heterologous proteins by culturing said recombinant yeast cells.

8 Claims, 7 Drawing Sheets

SIGNAL SEQUENCES FOR SECRETION OF HETEROLOGOUS PROTEINS FROM YEAST

FIELD OF THE INVENTION

The present invention relates to novel secretion signal peptides which facilitate the secretion of heterologous proteins produced in a yeast cell. More particularly, it pertains to secretion signal peptides of inulinase enzymes derived from *Kluyveromyces marxianus*, which cause heterologous proteins produced in a yeast cell to be secreted almost completely out of the cell; nucleotide sequences encoding said secretion signal peptides; expression and secretion vectors comprising nucleotide sequences encoding said secretion signal peptides; recombinant yeast cells transformed with said expression and secretion vectors; and a process for producing the heterologous proteins by culturing said recombinant yeast cells.

BACKGROUND OF THE INVENTION

Various proteins, especially those used as pharmaceuticals have been produced in yeasts, including the genus Saccharomyces, whose safety has been widely recognized (Marten & Seo, Chap. 7, *Expression Systems and Processes for rDNA Products*, ed. by Hatch et al., ACS Symp. Ser., 477 (1991)). The expression and secretion vectors used to produce and secrete desired proteins from yeast comprise a transcription promoting sequence(promoter), a DNA encoding a secretion signal peptide, a structural gene encoding a desired protein, and a transcription terminator.

As the transcription promoting sequence(promoter) for such vectors, there have been used PGK(Loison et al., Korean Patent Laid-open Publication Nos. 88-7727 and 88-700234 ; *Bio/Technol.*, 6, 72(1988)), GAPDH, mating factor-α(MFα-1), PHO5(Meyhack et al., Korean Patent Laid-open Publication Nos. 86-381 and 87-6185; *Genetics and Molecular Biology of Industrial Microorganisms*, ed. by Hershberger et al., published by American Society of Microbiology, pp. 311–312 (1989)), and GAL promoter series(Johnston, *Microbiol. Rev.*, 51, 458–476(1987)) such as GAL1 which are induced by galactose in the culture medium. However, under the control of PGK, GAPDH or MFα-1 promoter, a gene is expressed constitutively or expressed at the stationary phase of cell growth and only a small amount of protein is expressed therefrom; and, further, the stability of the plasmid containing such promoters is likely to be decreased during the culture. The PHO5 promoter induces the expression of a gene when the concentration of phosphate in a medium is low; however, it is a complicated and burdensome procedure to lower the concentration of phosphate in a medium during the fermentation of recombinant yeast. For these reasons, GAL series promoters might be preferably used in regulating the heterologous gene expression.

Secretion signal peptides currently used for the secretion of heterologous proteins from yeast include an invertase signal peptide(U.S. Pat. No. 5,010,003), an acid phosphatase signal peptide(U.S. Pat. No. 5,013,652), a prepro leader peptide(ppL) of mating factor-α(U.S. Pat. No. 4,588,684), etc. Among these various secretion signal peptides, the ppL is most widely used.

While carrying out the study on the secretion of human lipocortin-I(346 amino acids) and human interleukin-2(133 amino acids) from yeast by using ppL as a secretion signal peptide, the present inventors have found that a considerable amount of lipocortin-I and interleukin-2 remains in the cell. Zsebo et al. also reported in *J. Biol. Chem.*, 261, 5858–5865 (1986) that β-endorphin consisting of 31 amino acids and calcitonin consisting of 32 amino acids were secreted completely out of yeast cells, whereas α-interferon consisting of 166 amino acids remained in the cell up to 95% when the ppL was used as the secretion signal peptide. This indicates that ppL is not suitable as a secretion signal peptide for the secretion of proteins having a relatively high molecular weight.

On the other hand, *Kluyveromyces marxianus* is one of the yeasts belonging to genus Ascomycetes and is capable of secreting a large amount of proteins such as inulinase, β-galactosidase, alcohol dehydrogenase, etc.(Kreger-van Rij, *The Yeasts: A Taxonomic Study*, 3rd ed., 233–236(1984), Elsevier, Amsterdam). Laloux et al. reported in *FEBS Lett.*, 289, 64–68(1991) that the inulinase is secreted by 40% when produced in *Kluyveromyces marxianus* and by 70% when produced in a recombinant *Saccharomyces cerevisiae*. The latter result was also confirmed by Jung-Han Koh in his doctorate thesis (*Studies on the Extracellular Secretion of Proteins in Yeast*, Dept. of Agric. Chem., The University of Tokyo, 1990).

The present inventors have endeavored to develop a novel secretion signal peptide which facilitates the secretion of recombinant proteins having a relatively high molecular weight out of a recombinant yeast cell. As a result, it has been discovered that novel nucleotide sequences encoding the secretion signal peptides of inulinase enzymes derived from *Kluyveromyces marxianus* cause high molecular weight proteins expressed in a yeast cell to be secreted almost completely out of the cell.

SUMMARY OF THE INVENTION

Accordingly, it is an object of the present invention to provide novel secretion signal peptides which facilitate the secretion of heterologous proteins into the extracellular medium of yeast.

Another object of the present invention is to provide polynucleotides encoding said secretion signal peptides.

An additional object of the present invention is to provide expression and secretion vectors comprising: said polynucleotide encoding said secretion signal peptide; a DNA sequence capable of promoting transcription in a yeast located upstream from the polynucleotide encoding said secretion signal peptide; a site for insertion of a heterologous DNA sequence encoding a desired heterologous protein in translation reading frame with the polynucleotide encoding said secretion signal peptide; a heterologous DNA sequence inserted in the site; and, a transcription terminator sequence located downstream from the site for insertion of the heterologous DNA sequence.

A further object of the present invention is to provide recombinant yeast cells which are transformed with said expression and secretion vectors and can secrete the desired heterologous protein, when expressed with said signal peptides, almost completely into the extracellular medium.

A still further object of the present invention is to provide a process for producing a heterologous foreign protein in a yeast cell, which comprises culturing the recombinant yeast cell and recovering the heterologous protein from the culture medium.

BRIEF DESCRIPTION OF THE DRAWINGS

The above and other objects and features of the present invention will become apparent from the following description of the invention taken in conjunction with the accompanying drawings, in which.

DETAILED DESCRIPTION OF THE INVENTION

Figure 1:
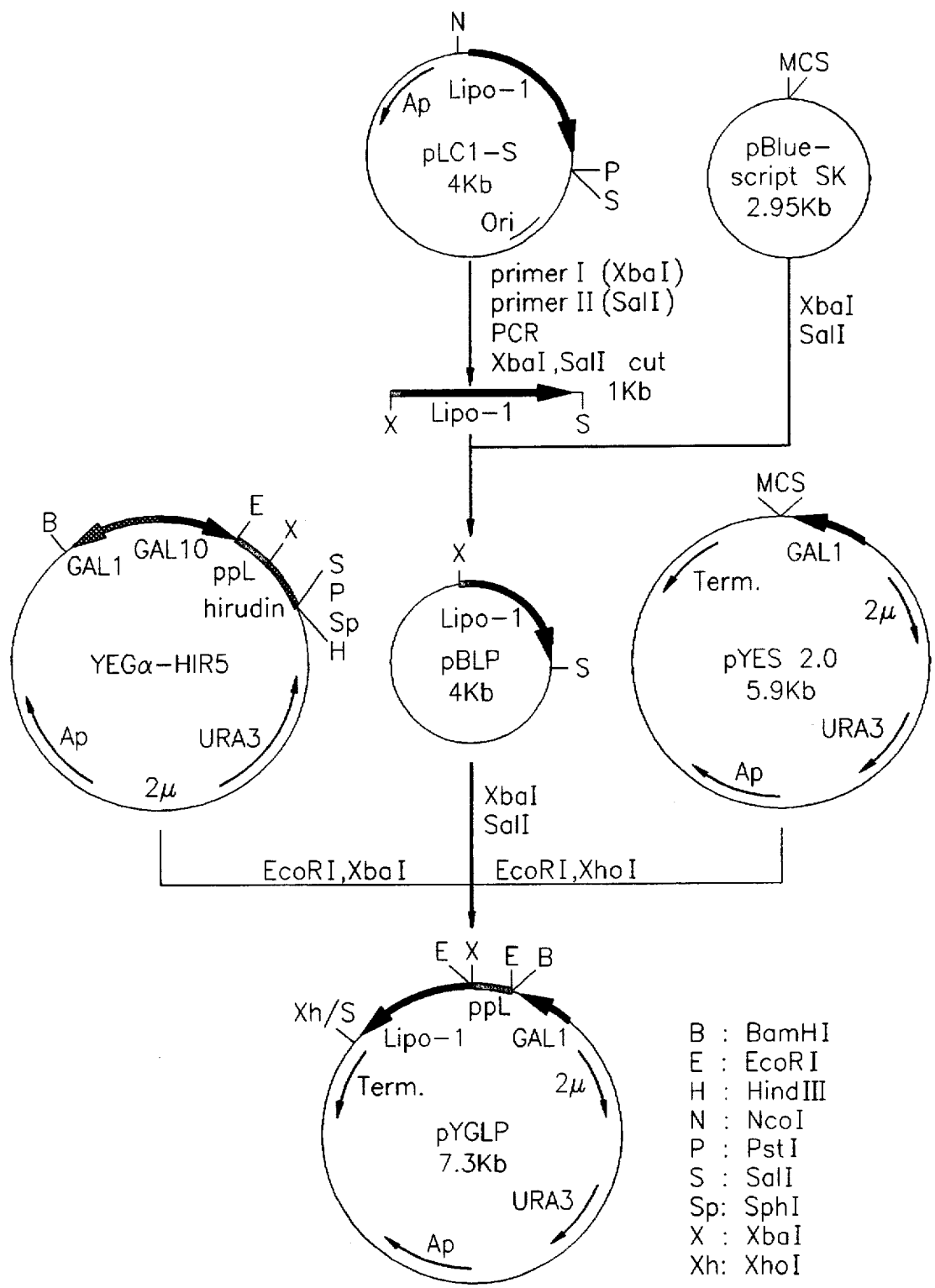
FIG. 1 shows a schematic diagram for constructing plasmid pYGLP coding for the prepro leader signal of mating factor-α and human lipocortin-I.

All references and patent documents cited herein are hereby incorporated in their entirety by reference.

The present invention will now be more specifically illustrated hereinbelow.

1. Novel Secretion Signal peptides

When comparing the nucleotide sequences and amino acid sequences of inulinases derived from *Kluyveromyces marxianus* ATCC 12424 (see Laloux et al., supra, and J. H. Koh, supra), it is found that 7 amino acids, 27 nucleotides within the open reading frame(ORF) encoding inulinases and many nucleotide sequences in upstream and downstream of the ORF regions are different from each other even though they were derived from the same strain. On the basis of this fact, the inulinase gene cloned by Laloux et al. is designated as INU1 and the inulinase gene cloned by J. H. Koh is designated as INU1A. The phenomenon that more than two kinds of inulinase genes are present in the same strain is due to the diploid copies of gene in a diploid yeast cell(see J. H. Koh, supra).

In this context, the present inventors have found novel secretion signal peptides on the basis of the fact that all of the mature inulinases secreted out of *K. marxianus*(see Rouwenhorst et al., *Appl. Environ. Microbiol.*, 56, 3337–3345 (1990)) and a recombinant *S. cerevisiae* (see Laloux et al., supra) have a common feature that their N-terminals begin with the 24th amino acid; the 22nd and the 23rd amino acids of proteins encoded in the inulinase genes INU1 and INU1A are lysine and arginine, respectively; the sequence of lysine-arginine is the cleavage site of endoprotease yscF(KEX2 gene product) of *Saccharomyces cerevisiae*(see Julius et al., *Cell*, 37, 1075–1089(1984)); and the polypeptide consisting of from the 1st amino acid, i.e., methionine, to the 23rd amino acid, i.e., arginine of the protein encoded in the inulinase genes INU1 or INU1A, is a putative secretion signal peptide.

The amino acid sequences of the novel secretion signal peptides of the present invention, consisting of from the 1st to the 23rd amino acid of the protein encoded in the inulinase genes, are preferably as follows:

N - Met Lys Z Ala Tyr Ser Leu Leu Leu Pro Leu Ala Gly Val Ser Ala Ser Val Ile Asn Tyr Lys Arg - C

In the above sequence, Z represents leucine(Leu) in case of INU1A(SEQ ID NO: 1) and phenylalanine(Phe) in case of INU1(SFQ ID NO: 2).

In addition, the representative polynucleotides encoding the novel secretion signal peptides of the present invention consisting of from the 1st to the 69th nucleotide of the inulinase genes(SEQ ID NO: 3) are as follows:

5'- ATG AAG TTM GCA TAC TCC CTC TTG CTT CCA TTG GCA GGA GTC AGT GCT TCA GTK ATC AAT TAC AAG AGA -3'

In the above sequence, M and K represent A and T, respectively, in case of INU1A; and, C and G, respectively, in case of INU1.

On the other hand, any amino acid substitutions, additions or deletions may occur in the above amino acid sequences, and such changes are within the scope of the present invention as long as the resulting amino acid sequences are functionally equivalent with the original sequence. The term "functionally equivalent" means that the variant sequence will efficiently direct the secretion of heterologous proteins from yeast.

In addition, there may be many potential nucleotide sequences that can code for the same amino acid sequence because of the degeneracy of the genetic codes or because of the codon usage in yeast genes, and the polynucleotides can be chemically synthesized or be prepared by separating same from the inulinase gene. Thus, included within the scope of the present invention are secretion signal peptides encoded by naturally occurring alleles of the inulinase gene.

Moreover, the present invention also includes polypeptides and polynucleotides which are substantially identical to SEQ ID NO's 1, 2, and 3, and which are functionally equivalent with these sequences. As applied to polypeptides, the term "substantial identity" means that two peptide sequences, when optimally aligned, such as by computerized implementations of known algorithms(e.g., GAP, BESTFIT, FASTA and TFASTA in the Wisconsin Genetics Software Package, Genetics Computer Group(GCG), 575 Science Dr., Madison, Wis., or BlastN and BlastX available from the National Center for Biotechnology Information using default parameters), or by inspection, share at least 70% or 80% sequence identity, preferably at least 90% sequence identity, more preferably 95% sequence identity or more (e.g., 99% sequence identity). Preferably, residue positions which are not identical may differ by conservative amino acid changes. Conservative amino acid substitutions refer to the interchangeability of residues having similar side chains. For example, a group of amino acids having aliphatic side chains is glycine, alanine, valine, leucine and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chains is cystein and methionine.

Substantial identity of polynucleotide sequences means that the polynucleotides, when optimally aligned as described above for a polypeptide sequence, comprise sequences that have at last 70% sequence identity, preferably at least 80%, more preferably at least 90% and most preferably at least 95%. Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point(Tm) for the specific sequence at a defined ionic strength and pH. The Tm is the temperature(under defined ionic strength and pH) at which 50% of the target sequence hybridizes to a perfectly matched probe. The Tm of a hybrid, which is a function of both the length and the base composition of the probe, can be calculated using information provided in Sambrook, T. et al., 1989, *Molecular Cloning—A Laboratory Manual*, 2nd ed. Vol. 1–3, Cold Spring Harbor Laboratory, Cold Spring Harbor. Typically, stringent conditions for a Southern blot protocol involve washing at 65° C. with 0.2×SSC.

2. Recombinant Expression and Secretion Vectors and Transformants

The novel secretion signal peptides of the present invention may be widely used in a vector system, for example, yeast vectors such as YEp 352(see Hill et al., *Yeast*, 2, 163 (1986)), pYES 2.0(Invitrogen Co. U.S.A), etc. to secrete the desired protein efficiently into the extracellular medium. Vectors may be designed to replicate autonomously, or to incorporate into the yeast chromosome. The recombinant expression and secretion vector is prepared by ligating the final codon of the DNA encoding said secretion signal peptide in translation reading frame to a DNA sequence encoding a desired protein.

Exemplary recombinant expression and secretion vectors may include: plasmid pYGILP-1, pYGILP-2, pYGILP-3 and pYGILP-4, which were prepared by ligating lipocortin-I gene and the DNA encoding said secretion signal peptides into a plasmid; and, plasmid pYGI-IL2 and pYGI-IL2F, which were prepared by ligating interleukin-2 gene and the DNA encoding said secretion signal peptide into a plasmid. Depending on the desired proteins, the promoters, the transcription terminators and the replication systems employed, there may exist various combinations of recombinant expression and secretion vectors.

The desired proteins which may be produced by using the recombinant expression and secretion vectors may include lipocortins, interferons, interleukins, colony stimulating factors, prourokinase, urokinase, tissue plasminogen activators, lysozyme, insulin, factor VIII, hirudin, superoxide dismutase, calcitonin, insulin-like growth factors, epidermal growth factor, growth hormones, etc.

A yeast cell may be transformed by using the recombinant expression and secretion vector in accordance with a conventional method, e.g., as described in *Laboratory Course Manual for Methods in Yeast Genetics*(ed. F. Sherman, G. R. Fink and J. B. Hicks, Cold Spring Harbor Laboratory(1986) ). As a host cell, there may be used various yeast cells belonging to the genera Saccharomyces, Schizosaccharomyces, Kluyveromyces, Hansenula, Yarrowia and Pichia, preferably, *Saccharomyces cerevisiae*. In this case, a replication system compatible with the host cell could be employed. The transformed yeast cells are cultured on a medium and under a condition suitable for the production of the desired protein, which are selected depending on the host cell and the expression system employed, and the desired protein may be obtained by purifying the secreted protein from the culture medium.

The following Examples are intended to further illustrate the present invention without limiting its scope; and the experimental methods used in the Examples can be practiced in accordance with the Comparative Examples given herein below, unless otherwise stated.

Further, percentages given below for solids in solid mixtures, liquids in liquids and solids in liquids are on a wt/wt, vol/vol and wt/vol basis, respectively, unless specifically indicated otherwise.

COMPARATIVE EXAMPLE 1

(step 1)

To amplify the structural gene of lipocortin-I and to make restriction enzyme sites of XbaI and SalI, primers (I) and (II) having the following nucleotide sequences were synthesized by using a DNA synthesizer(Applied Biosystems, Model 391, U.S.A.):

Primer (I) (SEQ ID NO: 4):
5'- CGCCGTCTAG ATAAAAGGAT GGCAATGGTA TCAG - 3'

Primer (II) (SEQ ID NO: 5):
5'- TCTTCTGATC ATAGCTGTCG ACCATCAAGG GAATGT - 3'

To a mixture of 1 µl (100 pmoles) of each of primers (I) and (II), 2 ng of plasmid pLC1-S(KCTC 8418P) as a template DNA, 10 µl of 10-fold polymerase reaction buffer (Boehringer Mannheim) and 10 µl of 10-fold dNTP mixture (2mM of each of dGTP, dATP, dTTP and dCTP, Boehringer Mannheim) were added distilled water to a total volume of 100 µl; and 100 µl of mineral oil(Sigma, U.S.A.) was added thereto to prevent the reaction mixture from being evaporated.

The reaction mixture was heated at 95° C. for 5 minutes and then cooled to 72° C. 1 µl(5 units) of Taq DNA polymerase (Boehringer Mannheim) was added to the mixture to carry out polymerase chain reaction(PCR) by using EZ cycler(Ericomp Inc., U.S.A.) by repeating 25 times of the cycle consisting of: 94° C. for 1 minute, 55° C. for 2 minutes and then 72° C. for 3 minutes.

0.1 µg of a DNA fragment(about 1,060 base pairs(bp)) obtained by the above PCR was digested with XbaI and SalI. The resulting fragment was ligated with plasmid pBluescript SK(Stratagene, U.S.A.) which was pre-digested with XabI/SalI, to construct plasmid pBLP. The plasmid pBLP was digested with XbaI and SalI to obtain about 1,050 bp of a DNA fragment containing polynucleotide encoding the lipocortin-I gene(fragment 1).

Plasmid YEGα-HIR5(KCTC 8518P) was digested with EcoRI and XbaI to obtain about 300 bp of a DNA fragment containing ppL(fragment 2).

About 5,900 bp of a DNA fragment obtained by digesting plasmid pYES 2.0(Invitrogen Co., U.S.A.) with EcoRI and XhoI was ligated with fragment 1 and fragment 2 to construct plasmid pYGLP. The plasmid pYGLP comprises GAL1promoter, a polynucleotide encoding the ppL signal peptide consisting of 85 amino acids from the initiation codon, lipocortin-I structural gene starting with ATG initiation codon and CYC1 transcription terminator, in this order. FIG. 1 shows a schematic diagram for the construction of plasmid pYGLP.

(Step 2)

*Saccharomyces cerevisiae* SEY2102(MATα ura3-52 leu2-3, -112 his4-519 suc2-α9; Emr et al., *Proc. Natl. Acad. Sci. U.S.A.*, 80, 7080–7084(1983)) was transformed with plasmid pYGLP prepared in (Step 1) above in accordance with the lithium chloride method of Ito et al. described in *J. Bacteriol.*, 153, 163–168(1983).

*Saccharomyces cerevisiae* SEY2102 was inoculated to 10 ml of YPD medium(1% yeast extract, 2% Bacto-peptone and 2% glucose) and cultured with shaking at 30° C. overnight. 100 µl of the culture was inoculated again in 10 ml of YPD medium and cultured with shaking at 30° C. until the optical density of the culture at 600 nm reached 1.0.

The resulting culture broth was centrifuged at 2,000 rpm for 5 minutes to remove the medium and obtain cell precipitates, which were then washed with 5 ml of TE buffer(10 mM Tris-Cl, pH8.0, 1 mM EDTA). The cell precipitates were suspended in a mixed solution of 0.5 ml of TE buffer and 0.5 ml of 0.2M lithium chloride(Sigma, U.S.A.) and then shaken at 30° C. for 1 hour. 100 μl of the suspension was transferred to an eppendorf tube and 0.1 μg of the plasmid prepared in (Step 1) was added thereto. The mixture was shaken at 30° C. for 30 minutes, 150 μl of the 70% polyethyleneglycol 4,000 was added thereto, and the resulting solution was shaken at 30° C. for 1 hour and then subjected to heat-shock at 48° C. for 10 minutes. The resultant was centrifuged at 15,000 rpm for 1 minute to remove the supernatant, and the precipitates were washed with saline solution containing 20 mg/l of ampicillin.

The yeast transformants, *S. cerevisiae* SEY2102/pYGLP, were selected on a minimal selection agar medium(0.67% Bacto-yeast nitrogen base without amino acids, 2% glucose, 0.003% leucine, 0.002% histidine, 2% Bacto-agar) at 30° C. for 4 days.

(Step 3)

(i) *S. cerevisiae* SEY2102(host cell) was cultured with shaking in 10 ml of YPD medium at 30° C. for 72 hours.

(ii) *S. cerevisiae* SEY2102/pYGLP obtained in (Step 2) was cultured with shaking in 10 ml of YPD medium at 30° C. for 72 hours.

(iii) *S. cerevisiae* SEY2102(host cell) was cultured with shaking in 10 ml of YPDG medium(1% yeast extract, 2% Bactopeptone, 0.4% glucose and 2% galactose) at 30° C. for 72 hours.

(iv) *S. cerevisiae* SEY2102/pYGLP obtained in (Step 2) was cultured with shaking in 10 ml of YPDG medium at 30° C. for 72 hours.

Example 1

To prepare a DNA segment encoding inulinase(INU1A) signal peptide, six oligonucleotide blocks(III–VIII) were synthesized by using a DNA synthesizer(Applied Biosystems, Model 391, U.S.A.). The DNA segment was designed to have cohesive ends of BglII and EcoRI at both ends for the easy ligation with the GAL1promoter and the lipocortin-I structural gene.

Oligonucleotide(III) (SEQ ID NO: 6):
5'-GA TCT ATG AAG TTA GCA TAC TCC CTC TTG-3'
Oligonucleotide(IV) (SEQ ID NO: 7):
3'-A TAC TTC AAT CGT ATG AGG GAG AAC GAA GGT-5'
Oligonucleotide(V) (SEQ ID NO: 8):
5'-CTT CCA TTG GCA GGA GTC AGT GCT TCA GTT-3'
Oligonucleotide(VI) (SEQ ID NO: 9):
3'-AAC CGT CCT CAG TCA CGA AGT CAA TAG TTA-5'
Oligonucleotide(VII) (SEQ ID NO: 10):
5'-ATC AAT TAC AAG AGA ATG GCA ATG GTA TCA G-3'
Oligonucleotide(VIII) (SEQ ID NO: 11):
3'-ATG TTC TCT TAC CGT TAC CAT AGT CTT AA-5'

The mixture of oligonucleotide blocks (III)–(VIII) [each 1 μl(100 pmoles)]was phosphorylated by T4 polynucleotide kinase(Boehringer Mannheim) at 37° C. for 2 hr. Thereafter, the reaction was stopped by incubating it at 65° C. for 20 minutes. 10 μl(10 units) of T4 DNA ligase(Boehringer Mannheim) was added to the reaction mixture, and the mixture was reacted at 14° C., overnight. The resulting reaction mixture was electrophoresed on 10% agarose gel. Fragment of 100 bp was cut out of the gel and extracted from the gel by electroelution(fragment 3). Plasmid pBLP prepared Comparative Example 1 was digested with EcoRI and SalI to obtain about 1,030 bp of a DNA fragment containing the lipocortin-I gene(fragment 4).

About 5,900 bp DNA fragment(fragment 5) obtained by digesting plasmid pYES 2.0(Invitrogen, U.S.A.) with BamHI and XhoI was ligated with fragment 3 and fragment 4 to obtain plasmid pYGILP-1; and *Saccharomyces cerevisiae* SEY2102 was transformed with the resulting plasmid pYGILP-1 by employing the same method as described in (Step 2) of Comparative Example 1. *Saccharomyces cerevisiae* SEY2102 transformed with the plasmid pYGILP-1 was deposited at the Korean Collection for Type Cultures (KCTC), Genetic Engineering Research Institute, Korea Institute of Science and Technology, Daejeon, Republic of Korea, on Sep. 14, 1993 with the accession number of KCTC 0085BP under the terms of the Budapest Treaty on the International Recognition of the Deposit of Microorganisms for the Purpose of Patent Procedure.

Figure 2:
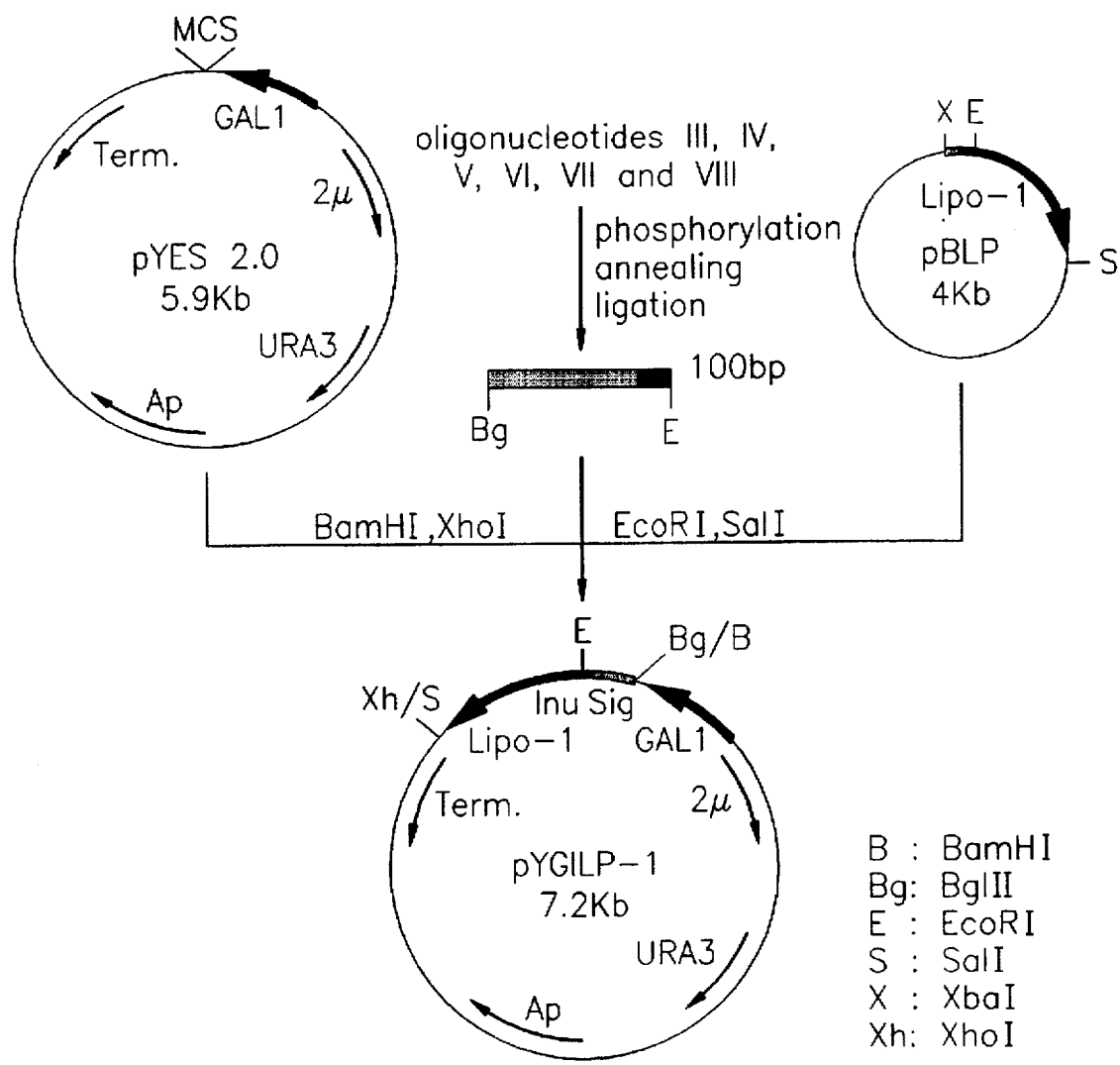
FIG. 2 depicts a schematic diagram for constructing plasmid pYGILP-1 coding for the inulinase signal and human lipocortin-I.

FIG. 2 shows a schematic diagram for the construction of plasmid pYGILP-1.

Example 2

Oligonucleotide (IX) and (X) having the sequences given below were synthesized by using a DNA synthesizer (Applied Biosystems, Model 391, U.S.A.):

Oligonucleotide (IX) (SEQ ID NO: 12):
5'-GA TCT ATG AAG TTC GCA TAC TCC CTC TTG-3'

Oligonucleotide (X) (SEQ ID NO: 13):
3'-A TAC TTC AAG CGT ATG AGG GAG AAC GAA GGT-5'

The mixture of oligonucleotide blocks (V),(VI),(VII), (VIII),(IX) and (X)[each 1 μl (100 pmoles)] was phosphorylated and ligated as in Example 1. The resulting reaction mixture was electrophoresed on 10% agarose gel. 100 bp DNA fragment encoding INU1 signal was cut out of the gel and extracted from the gel by electroelution (fragment 6).

Fragment 6 was ligated with fragment 4 and fragment 5 obtained in Example 1; and *Saccharomyces cerevisiae* SEY2102 was transformed with the resulting plasmid pYGILP-2, in which the 9th nucleotide, A, of the polynucleotide encoding the INU1A secretion signal peptide contained in the plasmid pYGILP-1 was replaced with C(3rd amino acid, Leu, of INU1A was replaced with Phe), by employing the same method as described in (Step 2) of Comparative Example 1.

Example 3

Oligonucleotide (XI) and (XII) having the sequences given below were synthesized by using a DNA synthesizer (Applied Biosystems, Model 391, U.S.A.):

Oligonucleotide (XI) (SEQ ID NO: 14):
5'-CTT CCA TTG GCA GGA GTC AGT GCT TCA GTG - 3'

Oligonucleotide (XII) (SEQ ID NO: 15):
3'-AAC CGT CCT CAG TCA CGA AGT CAC TAG TTA-5'

The mixture of oligonucleotide blocks (III), (IV), (VII), (VIII), (XI) and (XII) [each 1 μl(100 pmoles)] was phosphorylated and ligated as in Example 1. The resulting reaction mixture was electrophoresed on 10% agarose gel. 100 bp DNA fragment was cut out of the gel and extracted from the gel by electroelution(fragment 7).

Fragment 7 was ligated with fragment 4 and fragment 5 obtained in Example 1; and *Saccharomyces cerevisiae* SEY2102 was transformed with the resulting plasmid pYGILP-3, in which the 54th nucleotide, T, of the polynucleotide encoding the INU1A secretion signal peptide contained in the plasmid pYGILP-1 was replaced with G, by employing the same method as described in (Step 2) of Comparative Example 1.

Example 4

The mixture of oligonucleotide blocks (VII), (VIII), (IX), (X), (XI) and (XII) [each 1 µl(100 pmoles)] was phosphorylated and ligated as in Example 1. The resulting reaction mixture was electrophoresed on 10% agarose gel. A 100 bp DNA fragment encoding INU1 signal was cut out of the gel and extracted from the gel by electroelution(fragment 8).

The obtained DNA fragment 8 and fragment 4 of Example 1 were inserted into the BamHI/XhoI site of pYES 2.0 to construct plasmid pYGILP-4 in which the 9th, A, and the 54th, T, nucleotides of the polynucleotide encoding the secretion signal peptide contained in plasmid pYGILP-1 were replaced with C and G, respectively. *Saccharomyces cerevisiae* SEY2102 transformed with plasmid pYGILP-4 was obtained by employing the same method as in (Step 2) of the Comparative Example 1.

The DNA sequence of the inulinase signal and lipocortin-I gene was confirmed by the dideoxy-chain termination method(Sanger et al., *Proc. Natl. Acad. Sci. U.S.A.*, 74, 5463–5476 (1977)).

Example 5

The same procedures as in (Step 3) (i) of Comparative Example 1 were repeated except that *S. cerevisiae* SEY2102/pYGILP-1 was used in place of *S. cerevisiae* SEY2102.

Example 6

The same procedures as in (Step 3) (iii) of Comparative Example 1 were repeated except that *S. cerevisiae* SEY2102/pYGILP-1 was used in place of *S. cerevisiae* SEY2102.

Example 7

The same procedures as in (Step 3) (i) of Comparative Example 1 were repeated except that *S. cerevisiae* SEY2102/pYGILP-2 was used in place of *S. cerevisiae* SEY2102.

Example 8

The same procedures as in (Step 3) (iii) of Comparative Example 1 were repeated except that *S. cerevisiae* SEY2102/pYGILP-2 was used in place of *S. cerevisiae* SEY2102.

Example 9

2 ml of each of the cultures obtained in (Step 3) (i) to (iv) of Comparative Example 1 and Examples 5 to 8 was centrifuged at 2,000 rpm for 5 minutes to separate the culture medium and the cell precipitates.

In accordance with the method of Demolder et al. described in *J. Biotechnol.*, 32, 179–189(1994)), 200 µl of 0.2% sodium deoxycholate(Sigma, U.S.A.) was added to the culture medium and the resulting mixture was allowed to stand at room temperature for 5 minutes followed by the addition of 200 µl of 100% trichloroacetic acid. The resulting solution was allowed to stand at 0° C. for 30 minutes and then centrifuged at 15,000 rpm for 10 minutes to obtain protein precipitates. Each of the precipitates was washed with 500 µl of acetone, dissolved in 10 µl of a lysis buffer(50 mM Tris-Cl, pH 6.8, 100 mM dithiothreitol, 2% SDS, 5% 2-mercaptoethanol, 0.1% bromophenol blue and 10% glycerol) and then heated at 100° C. for 5 minutes. The resulting solution was named as a culture medium protein fraction.

In accordance with the method of Hoffman & Winston described in *Gene*, 57, 267(1987)), each of the cell precipitate was dissolved in 2 ml of a disruption solution(2% Triton X-100, 1% SDS, 100 mM NaCl, 10 mM Tris-Cl, pH 8.0, 1 mM EDTA) and disrupted by using glass beads having diameter of 0.4 to 0.5 mm. To the resulting cell homogenate was added 0.5 ml of 5-fold concentrated lysis buffer, and the mixture was heated at 100° C. for 5 minutes. The resulting solution was named as a cellular protein fraction.

10 µl of each of the culture medium protein fractions and the cellular protein fractions was subjected to SDS-PAGE at 100 to 200 volts, 30 mA for 3 hours, on a SDS-polyacrylamide gel consisting of 5% stacking gel(pH 6.8, 20 cm ×3.0 cm ×1 mm) and 10% separating gel(pH 8.8, 20 cm ×10 cm ×1 mm). The polyacrylamide gel was stained in a Coomassie blue staining solution(10% isopropanol, 10% acetic acid and 0.05% Coomassie Brilliant Blue R-250) for 5 hours and then destained in a destaining solution(10% isopropanol and 10% acetic acid) for 5 hours(FIG. 3).

Figure 3:
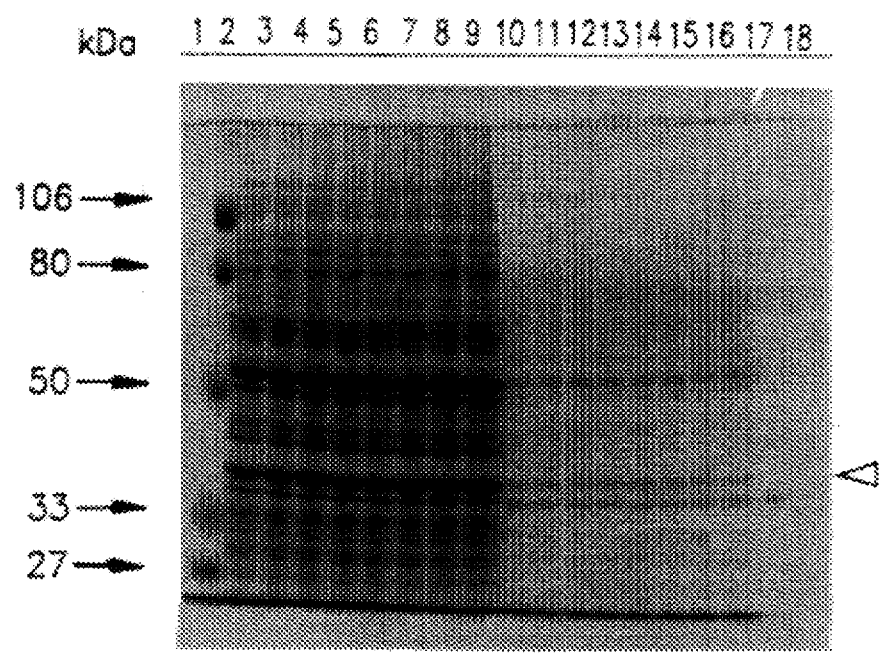
FIG. 3 represents the result of sodium dodecyl sulfate-polyacrylamide gel electrophoresis(SDS-PAGE) by using the cellular proteins and culture medium proteins of the host cell and of the recombinant yeast cell producing human lipocortin-I.

In FIG. 3, lane 1 shows the prestained standard molecular weight marker proteins(BIO-RAD, U.S.A.), i.e., 106, 80, 50, 33 and 27 kilodaltons(kDa) from the top of the gel;

lane 2 shows the cellular protein of (Step 3) (i) of the Comparative Example 1;

lane 3 shows the cellular protein of (Step 3) (iii) of the Comparative Example 1;

lane 4 shows the cellular protein of (Step 3) (ii) of the Comparative Example 1;

lane 5 shows the cellular protein of (Step 3) (iv) of the Comparative Example 1;

lane 6 shows the cellular protein of Example 5;

lane 7 shows the cellular protein of Example 6;

lane 8 shows the cellular protein of Example 7;

lane 9 shows the cellular protein of Example 8;

lane 10 shows the culture medium protein of (Step 3) (i) of the Comparative Example 1;

lane 11 shows the culture medium protein of (Step 3) (iii) of the Comparative Example 1;

lane 12 shows the culture medium protein of (Step 3) (ii) of the Comparative Example 1;

lane 13 shows the culture medium protein of (Step 3) (iv) of the Comparative Example 1;

lane 14 shows the culture medium protein of Example 5;

lane 15 shows the culture medium protein of Example 6;

lane 16 shows the culture medium protein of Example 7;

lane 17 shows the culture medium protein of Example 8; and lane 18 shows 0.1 µg of the purified lipocortin-I.

The purified lipocortin-I of lane 18 in FIG. 3 was obtained by culturing *Saccharomyces cerevisiae* SEY2102/pYGLP in YPDG medium for 48 hours, purifying the supernatant firstly by SP cation exchange chromatography and then secondly by G-75 gel filtration chromatography.

As shown in FIG. 3, no band corresponding to lipocortin-I (about 37 kDa, lane 18) was found either in the culture medium protein or in the cellular protein. This result means either that lipocortin-I was not expressed at all or that the expressed amount is too small to be detected by Coomassie blue staining, if any; and, therefore, another analysis employing a Western blotting was further carried out to confirm the result.

Example 10

In accordance with the method of Burnetle described in Anal. Biochem., 112, 195(1981), the proteins separated by the SDS-PAGE were blotted onto a nitrocellulose membrane (Promega, U.S.A.) without Coomassie staining by using a tank transfer unit(Hoefer, model TR-22) at 150 mA, 50 V for 1 hours. The proteins blotted on the membrane were reacted with 5,000-fold diluted rabbit anti-lipocortin polyclonal antibodies(Sohn et al., Kor. Biochem. J., 24, 453–460(1991)) for 30 minutes, and then the lipocortin-I bands were confirmed by a ProtoBlot Western blot AP System(goat anti-rabbit IgG{H+L or Fc}-alkaline phosphatase conjugate, Promega, U.S.A.).

Figure 4:
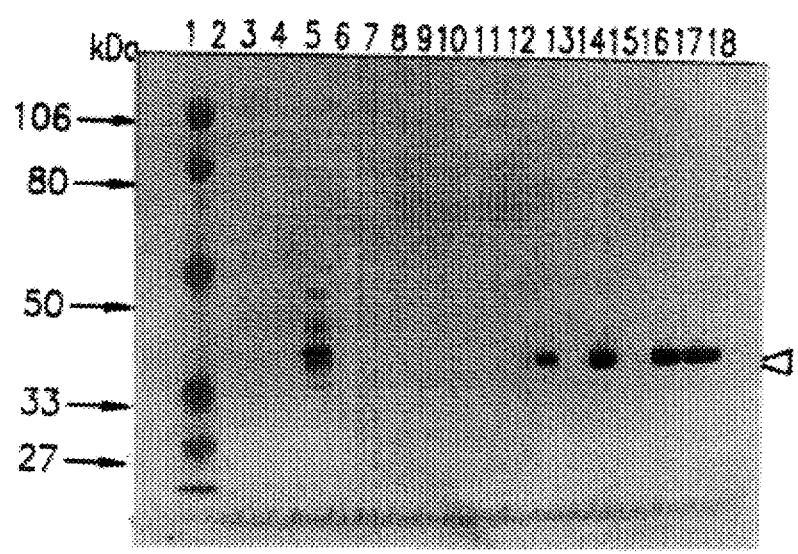
FIG. 4 discloses the result of Western blotting analysis with the cellular proteins and culture medium proteins of the host cell and of the recombinant yeast cell producing human lipocortin-I.

The results are shown in FIG. 4, wherein:

lane 1 shows the prestained standard molecular weight size marker proteins, i.e., 106, 80, 50, 33 and 27 kilodaltons(kDa) from the top of the gel;

lane 2 shows the cellular protein of (Step 3) (i) of the Comparative Example 1;

lane 3 shows the cellular protein of (Step 3) (iii) of the Comparative Example 1;

lane 4 shows the cellular protein of (Step 3) (ii) of the Comparative Example 1;

lane 5 shows the cellular protein of (Step 3) (iv) of the Comparative Example 1;

lane 6 shows the cellular protein of Example 5;

lane 7 shows the cellular protein of Example 6;

lane 8 shows the cellular protein of Example 7;

lane 9 shows the cellular protein of Example 8;

lane 10 shows the culture medium protein of (Step 3) (i) of the Comparative Example 1;

lane 11 shows the culture medium protein of (Step 3) (iii) of the Comparative Example 1;

lane 12 shows the culture medium protein of (Step 3) (ii) of the Comparative Example 1;

lane 13 shows the culture medium protein of (Step 3) (iv) of the Comparative Example 1;

lane 14 shows the culture medium protein of Example 5;

lane 15 shows the culture medium protein of Example 6;

lane 16 shows the culture medium protein of Example 7;

lane 17 shows the culture medium protein of Example 8; and lane 18 shows 0.1 µg of the purified lipocortin-I.

The purified lipocortin-I was obtained as in Example 9.

As shown in FIG. 4, no band corresponding to lipocortin-I (about 37 kDa, lane 18) was found either in the culture medium protein or in the cellular protein of (Step 3) (i) and (iii) of Comparative Example 1(lanes 2, 3, 10 and 11). The lipocortin-I band was found neither in the culture medium protein nor in the cellular protein of SEY2102/pYGLP cultured in YPD medium(lanes 4 and 12), while it was found both in the culture medium protein and in the cellular protein of SEY2102/pYGLP cultured on a YPDG medium(lanes 5 and 13). This result means that the lipocortin-I expressed in SEY2102/pYGLP was not completely secreted into the medium. In case of the SEY2102/pYGLP cultured in YPDG medium, the amounts of lipocortin-I on the gel were about 0.05 µg in the culture medium protein and about 0.7 µg in the cellular protein. Therefore, the secretion efficiency was only about 7%.

In case of SEY2102/pYGILP-1, the lipocortin-I band was found neither in the culture medium protein nor in the cellular protein when it was cultured on a YPD medium (Example 5, lanes 6 and 14), while the lipocortin-I band was found in the culture medium protein but not in the cellular protein when the expression of the lipocortin-I was induced by galactose, i.e., when the cells were cultured in YPDG medium(Example 6, lanes 7 and 15). In addition, in case of SEY2102/pYGILP-2, the lipocortin-I band was found neither in the culture medium protein nor in the cellular protein when it was cultured in YPD medium(Example 7, lanes 8 and 16), while the lipocortin-I band was found in the culture medium protein but not in the cellular protein when the expression of the lipocortin-I was induced by galactose (Example 8, lanes 9 and 17). This result indicates that by using the inulinase signal peptide almost all of the expressed lipocortin-I was secreted completely out of the cell and that the amount of the secreted lipocortin-I was much more than that secreted by using ppL signal peptide(see lanes 13, 15 and 17).

Examples 11 and 12

The same procedures as in (Step 3) (iii) of Comparative Example 1, Examples 9 and 10 were repeated except that S. cerevisiae SEY2102/pYGILP-3 or S. cerevisiae SEY2102/pYGILP-4was used in place of S. cerevisiae SEY2102.

The results so obtained were substantially identical to those of lanes 7 and 15, and lanes 9 and 17 of FIG. 4, respectively.

COMPARATIVE EXAMPLE 2

(Step 1)

To amplify the structural gene of interleukin-2 and to make restriction enzyme sites, primers (XIII) and (XIV) having the nucleotide sequences given below were synthesized by using a DNA synthesizer:

Primer (XIII) (SEQ ID NO: 16):

5'- CGCCGT CTAGATAAAAGA ATGGCG CCTACT TCAAGT TCTACA - 3

Primer (XIV) (SEQ ID NO: 17):

5'- TGTCGA CCATCA AGGGAA TGTTTA AGTTAG TGTTGA GAT - 3

The same PCR procedures as in Comparative Example 1 were repeated by using primer(XIII), (XIV) and plasmid pNKM21(Chung et al., Biotechnol. Tech., 5, 163–168 (1991)) as a template DNA to obtain about 400 bp DNA fragment encoding interleukin-2.

0.1 µg of the above DNA fragment was digested with XbaI(partial digestion) and SalI(fragment 9). Plasmid YEGα-HIR525(KCTC 8519P) was digested with BamHI and XbaI to obtain about 300 bp DNA fragment containing GAL10promoter and ppL(fragment 10).

Figure 5:
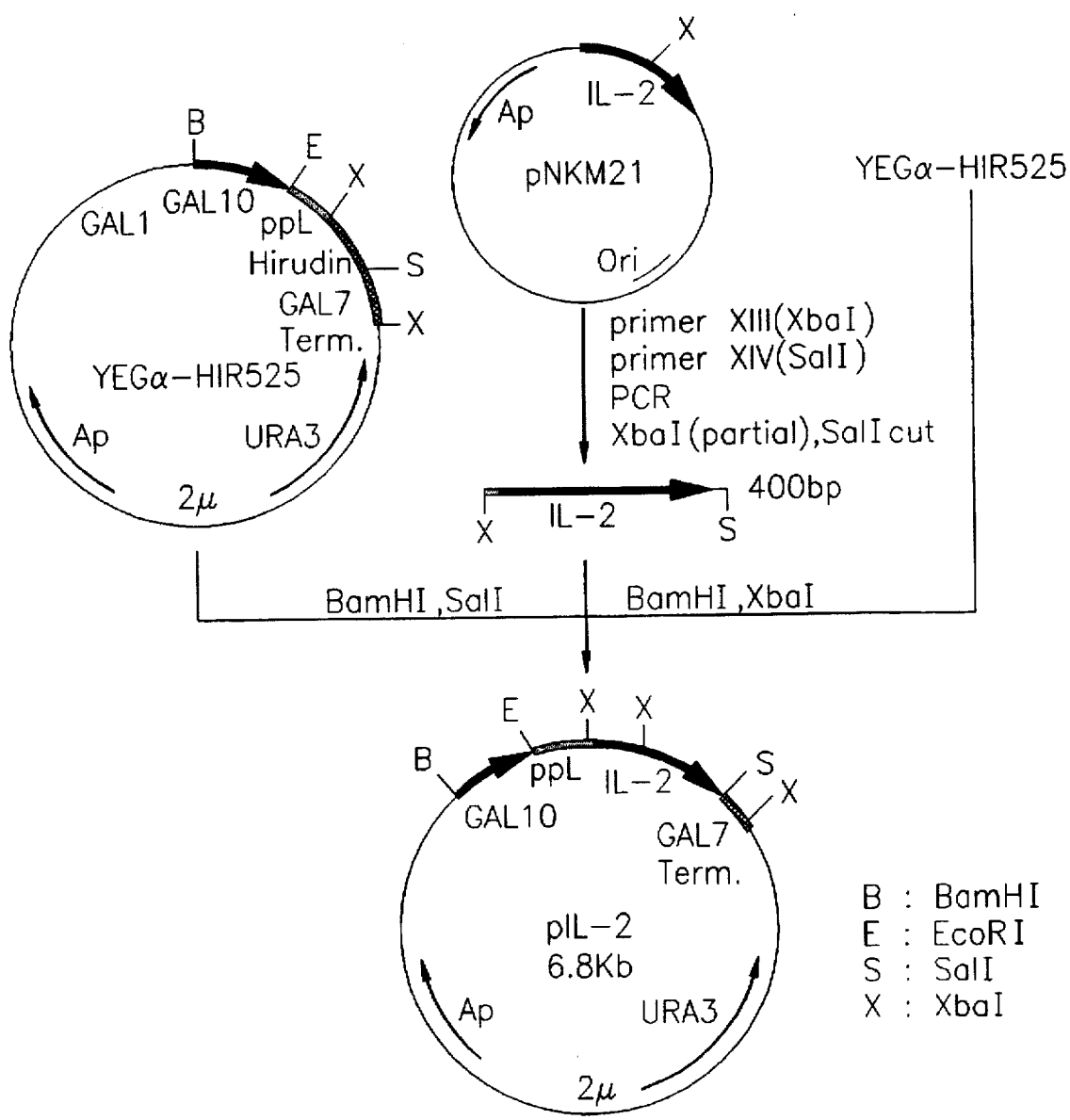
FIG. 5 shows a schematic diagram for constructing plasmid pIL-2 coding for the prepro leader signal of mating factor-α and human interleukin-2.

About 5,800 bp DNA fragment(fragment 11) obtained by digesting plasmid YEGα-HIR525 with BamHI and SalI was ligated with fragment 9 and fragment 10 to construct plasmid pIL-2. The plasmid pIL-2 consists of GAL10 promoter, polynucleotide encoding the ppL signal peptide comprising 85 amino acids from the initiation codon, the structural gene encoding mature interleukin-2 and GAL7 transcription terminator, in this order. FIG. 5 shows a schematic diagram for the construction of plasmid pIL-2.

(Step 2)

The same procedures as in (Step 2) of Comparative Example 1 were repeated except that plasmid pIL-2 was used in place of plasmid pYGLP, and the transformant of S. cerevisiaeSEY2102/pIL-2 was obtained.

(Step 3)

(i) The same procedures as in (Step 3) (iii) of the Comparative Example 1 were repeated except that S. cerevisiae SEY2102/pIL-2 was used in place of S. cerevisiae SEY2102.

(ii) The same procedures as in (Step 3) (iii) of the Comparative Example 1 were repeated except that S. cerevisiae SEY2102/pIL-2 was used in place of S. cerevisiae SEY2102.

Example 13

To prepare a DNA segment encoding INU1A signal peptide, oligonucleotides (XV),(XVI),(XVII) and (XVIII) having the sequences given below were synthesized by using a DNA synthesizer. The DNA segment was designed to have the cohesive ends of EcoRI and NarI at both ends for the easy ligation with the GAL10promoter and the interleukin-2 structural gene.

Oligonucleotide (XV) (SEQ ID NO: 18):

5'-AA TTC ATG AAG TTA GCA TAC TCC CTC TTG-3'

Oligonucleotide (XVI) (SEQ ID NO: 19):

3'-G TAC TTC AAT CGT ATG AGG GAG AAC GAA GGT-5'

Oligonucleotide (XVII) (SEQ ID NO: 20):

Oligonucleotide (XVIII) (SEQ ID NO: 21):

3'-ATG TTC TCC CGC-5'

The mixture comprising of oligonucleotide blocks (XV), (XVI), (XVII) and (XVIII), as well as oligonucleotides (V) and (VI) prepared in Example 1 [each 1 μl(100 pmoles)] was phosphorylated and ligated as in Example 1. The resulting reaction mixture was electrophoresed on 10% agarose gel. 80 bp DNA fragment encoding INU1A signal peptide was cut out of the gel and extracted from the gel by electroelution (fragment 12).

Fragment 9 of Comparative Example 2 was digested with NarI and SalI to obtain about 400 bp DNA fragment containing interleukin-2 structural gene(fragment 13).

Figure 6:
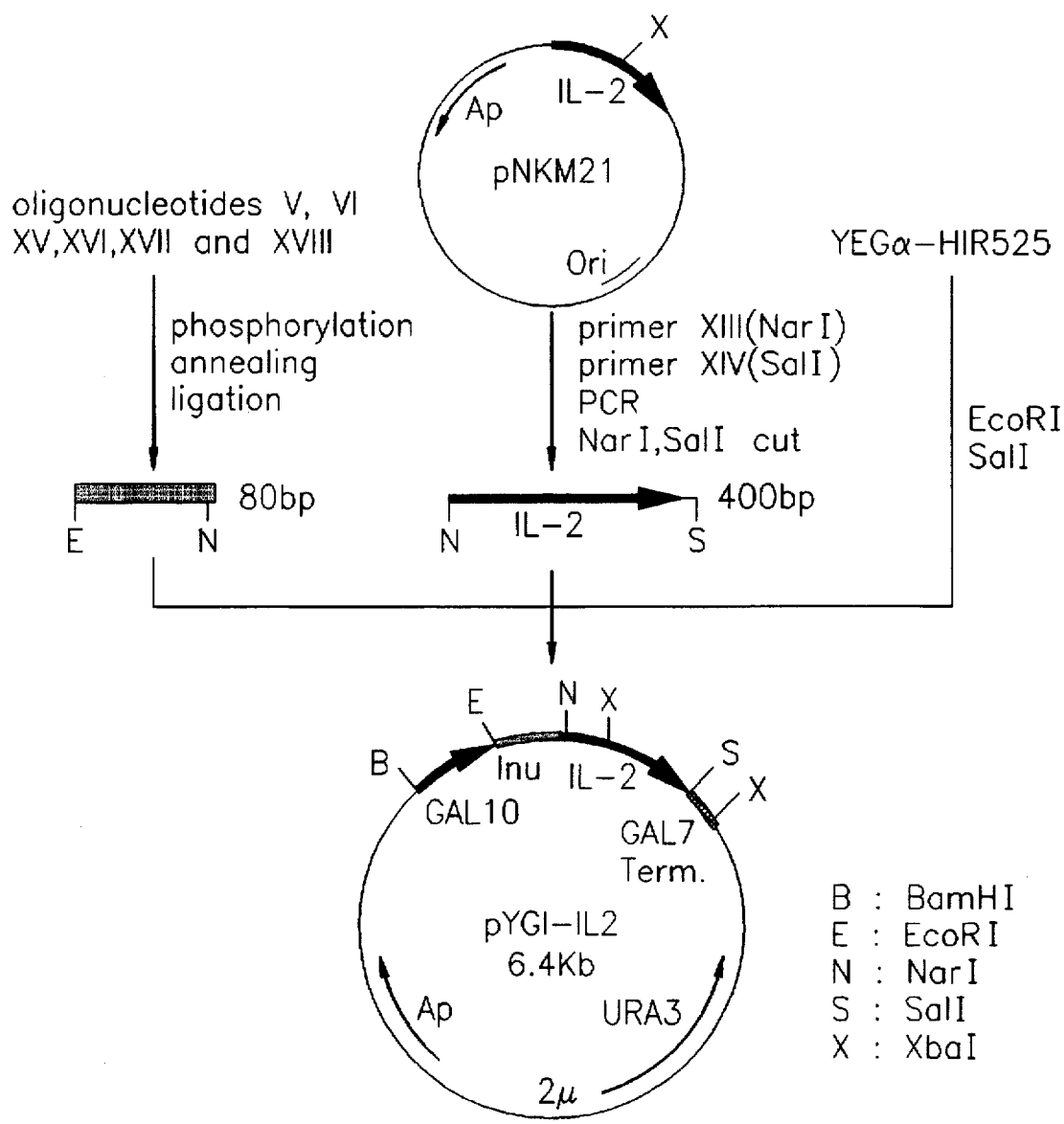
FIG. 6 depicts a schematic diagram for constructing plasmid pYGI-IL2 coding for the inulinase signal and human interleukin-2.

About 6,300 bp DNA fragment(fragment 14) obtained by digesting plasmid YEGα-HIR525 with EcoRI and SalI was ligated with fragment 12 and fragment 13 to construct plasmid pYGI-IL2. The plasmid pYGI-IL2 consisted of GAL10promoter, INU1A signal peptide encoding DNA sequence, interleukin-2 structural gene and GAL7 transcription terminator, in this order. FIG. 6 shows a schematic diagram for the construction of plasmid pYGI-IL2.

Example 14

To prepare a DNA segment encoding INU1 signal peptide, oligonucleotides (XIX) and (XX) having the following sequences were synthesized by using a DNA synthesizer:

Oligonucleotide (XIX) (SEQ ID NO: 22):

5'- AA TTC ATG AAG TTC GCA TAC TCC CTC TTG - 3'

Oligonucleotide (XX) (SEQ ID NO: 23):

3'- G TAC TTC AAG CGT ATG AGG GAG AAC GAA GGT - 5'

The mixture comprising oligonucleotide blocks (XIX) and (XX), oligonucleotides (XVII) and (XVIII) prepared in Example 13, and oligonucleotides (V) and (VI) prepared in Example 1 [each 1 μl(100 pmoles)] was phosphorylated and ligated as in Example 1. The resulting reaction mixture was electrophoresed on 10% agarose gel. 80 bp DNA fragment encoding INU1 signal peptide was cut out of the gel and extracted from the gel by electroelution(fragment 15). Fragment 14(Example 13) was ligated with fragment 13(Example 13) and fragment 15 to construct plasmid pYGI-IL2F. The plasmid pYGI-IL2F consists of GAL10promoter, INU1signal peptide-coding DNA sequence, interleukin-2 structural gene and GAL7 transcription terminator.

The DNA sequence of the inulinase signal and interleukin-2 gene was confirmed by the dideoxy-chain termination method(Sanger et al., Proc. Natl. Acad. Sci. U.S.A., 74, 5463–5476(1977)).

Example 15

The same procedures as in (Step 2) of Comparative Example 1 were repeated except that pYGI-IL2 and pYGI-IL2 F were used in place of pYGLP, and the transformant of S. cerevisiaeSEY2102 /pYGI-IL2 and S. cerevisiae SEY2102 /pYGI-IL2 F were obtained, respectively. S. cerevisiae SEY2102 /pYGI-IL2 was deposited at KCTC on Sept. 27, 1994 with the accession number of KCTC 0120BP under the terms of the Budapest Treaty on the International Recognition of the Deposit of Microorganisms for the Purpose of Patent Procedure.

Example 16

The same procedures as in (Step 3) (i) of Comparative Example 1 were repeated except that S. cerevisiae SEY2102 /pYGI-IL2 was used in place of S. cerevisiae SEY2102.

Example 17

The same procedures as in (Step 3) (iii) of Comparative Example 1 were repeated except that S. cerevisiae SEY2102 /pYGI-IL2 was used in place of S. cerevisiae SEY2102.

Example 18

The same procedures as in (Step 3) (i) of Comparative Example 1 were repeated except that S. cerevisiae SEY2102 /pYGI-IL2 F was used in place of S. cerevisiae SEY2102.

Example 19

The same procedures as in (Step 3) (iii) of Comparative Example 1 were repeated except that S. cerevisiae SEY2102 /pYGI-IL2 F was used in place of S. cerevisiae SEY2102.

Example 20

1 ml of each of the cultures obtained in (Step 3) (i) and (ii) of Comparative Example 2, Example 16 and Example 17 was centrifuged at 2,000 rpm for 5 minutes to separate the culture medium and the cell precipitates.

Figure 7:
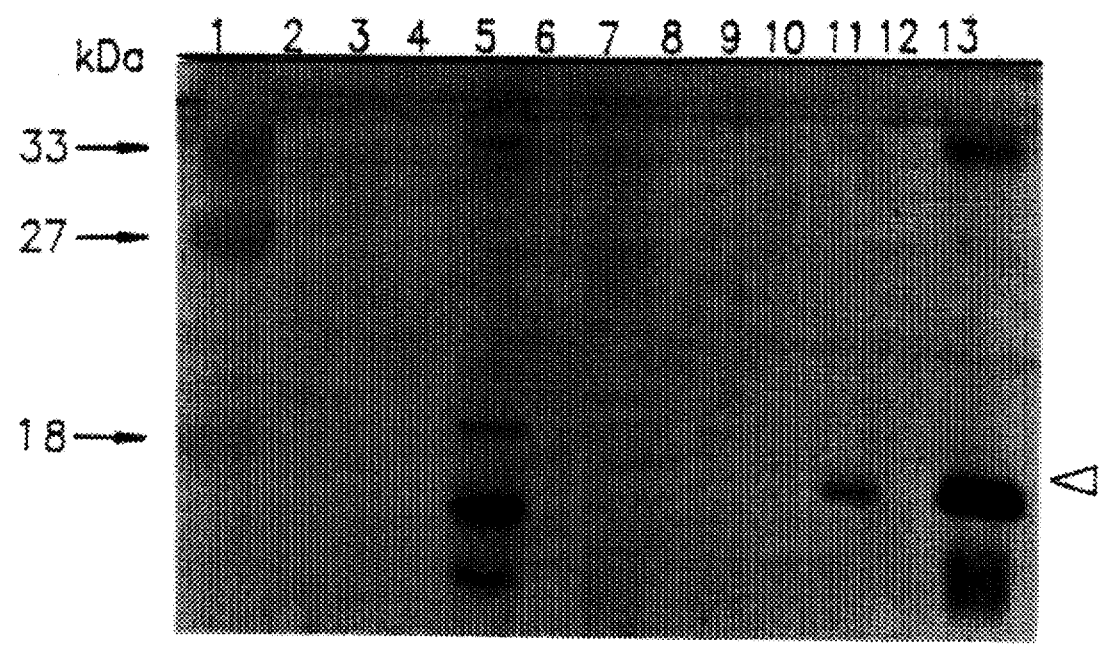
FIG. 7 discloses the result of Western blotting analysis with the cellular proteins and culture medium proteins of the host cell and of the recombinant yeast cell producing human interleukin-2.

After SDS-PAGE as in Example 9, Western blotting analysis as in Example 10 was performed with anti-interleukin-2 antibody (Boehringer Mannheim). The results are shown in FIG. 7, wherein:

lane 1 shows the prestained standard molecular weight size marker proteins, i.e., 33, 27 and 18 kilodaltons (kDa) from the top of the gel;

lane 2 shows the cellular protein of (Step 3) (i) of Comparative Example 1;

lane 3 shows the cellular protein of (Step 3) (iii) of Comparative Example 1;

lane 4 shows the cellular protein of (Step 3) (i) of Comparative Example 2;

lane 5 shows the cellular protein of (Step 3) (ii) of Comparative Example 2;

lane 6 shows the cellular protein of Example 16;

lane 7 shows the cellular protein of Example 17;

lane 8 shows the culture medium protein of (Step 3) (i) of Comparative Example 1;

lane 9 shows the culture medium protein of (Step 3) (iii) of Comparative Example 1;

lane 10 shows the culture medium protein of (Step 3) (i) of Comparative Example 2;

lane 11 shows the culture medium protein of (Step 3) (ii) of Comparative Example 2;

lane 12 shows the culture medium protein of Example 16; and lane 13 shows the culture medium protein of Example 17;

As shown in FIG. 7, no band corresponding to interleukin-2 (about 15 kDa) was found either in the culture medium protein or in the cellular protein of host cells(lanes 2, 3, 8 and 9). The interleukin-2 band was found neither in the culture medium protein nor in the cellular protein of SEY2102 /pIL-2 cultured in YPD medium(lanes 4 and 10), while it was found both in the culture medium protein and in the cellular protein of SEY2102 /pIL-2 cultured in YPDG medium(lanes 5 and 11). This result means that by using the ppL signal the expressed interleukin-2 was not completely secreted into the medium and the secretion efficiency was only about 10%.

In case of SEY2102 /pYGI-IL2 , the interleukin-2 band was found neither in the culture medium protein nor in the cellular protein when it was cultured in YPD medium(lanes 6 and 12), while the interleukin-2 bands were found only in the culture medium protein when the expression of the interleukin-2 was induced by galactose, i.e., when the cells were cultured in YPDG medium(lanes 7 and 13). This result indicates that by using the inulinase signal peptide the majority of interleukin-2 expressed was secreted completely out of the cell, and that the amount of the secreted interleukin-2 was much more than that secreted by using ppL signal peptide(see lanes 11 and 13).

When *S. cerevisiae* SEY2102 /pYGI-IL2 F cells were cultured in YPDG medium, the substantially identical results to those of *S. cerevisiae* SEY2102 /pYGI-IL2 were observed.

Therefore, as can be seen from the above Examples, the novel secretion signal peptides of the present invention greatly improve the secretion efficiency of heterologous proteins, e.g., human lipocortin-I and human interleukin-2 , in yeast.

While the invention has been described with respect to the above specific embodiments, it should be recognized that various modifications and changes which may be apparent to those skilled in the art to which the invention pertains may be made and also fall within the scope of the invention as defined by the claims that follow.

---

What is claimed is:

1. A recombinant expression and secretion vector for Saccharomyces cerevisiae comprising: a polynucleotide encoding a secretion signal peptide which comprises the amino acid sequence of SEQ ID NO:1 or 2; a DNA sequence which promotes transcription in a Saccharomyces cerevisiae cell, located upstream from the polynucleotide encoding the secretion signal peptide; a DNA sequence encoding lipocortin-I or interleukin-2 operably linked to the polynucleotide encoding the secretion signal peptide; and a transcription terminator sequence located downstream from the DNA sequence encoding lipocortin-I or interleukin-2.

2. The vector of claim 1, wherein the polynucleotide encoding the secretion signal peptide includes the nucleotide sequence of SEQ ID NO:3.

3. The vector of claim 1, which is plasmid pYGILP-1, pYGILP-2, pYGILP-3 or pYGILP-4.

4. The vector of claim 1, which is plasmid pYGI-IL2 or pYGI-IL2F.

5. A recombinant Saccharomyces cerevisiae cell transformed with the vector of claim 1, 3, or 4.

6. The recombinant Saccharomyces cerevisiae cell of claim 5, which is Saccharomyces cerevisiae SEY2102 transformed with plasmid pYGILP-1(KCTC 0085BP) or pYGI-IL2(KCTC 0120BP).

7. A process for producing lipocortin-I or interleukin-2 from a Saccharomyces cerevisiae cell, which comprises the steps of: culturing a recombinant Saccharomyces cerevisiae cell transformed with the vector of claim 1 and recovering said lipocortin-I or interleukin-2 from the culture medium.

8. A process for producing lipocortin-I or interleukin-2 from a Saccharomyces cerevisiae cell, which comprises the steps of: culturing a recombinant Saccharomyces cerevisiae cell transformed with the vector of claim 3 or 4 and recovering said lipocortin-I or interleukin-2 from the culture medium.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( D ) OTHER INFORMATION: from the 1st to the 23rd
           amino acids of the protein
           encoded in the inulinase genes ( x i ) SEQUENCE DESCRIPTION: SEQ ID NO: 1:

Met Lys Leu Ala Tyr Ser Leu Leu Leu Pro
             5                      10

Leu Ala Gly Val Ser Ala Ser Val Ile Asn
             15                     20

Tyr Lys Arg
     23

( 2 ) INFORMATION FOR SEQ ID NO:2:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear (ii) MOLECULE TYPE: protein (ix) FEATURE:
(D) OTHER INFORMATION: from the 1st to the 23rd
amino acids of the protein encoded
in the inulinase genes (xi) SEQUENCE DESCRIPTION: SEQ ID NO: 2:

```
Met Lys Phe Ala Tyr Ser Leu Leu Leu Pro
                  5                   10

Leu Ala Gly Val Ser Ala Ser Val Ile Asn
                 15                   20

Tyr Lys Arg
         23
```

(2) INFORMATION FOR SEQ ID NO:3:

(i) SEQUENCE CHARACTERISTICS:
(A) LENGTH: 69 base pairs
(B) TYPE: nucleic acid
(C) STRANDEDNESS: double
(D) TOPOLOGY: linear (ii) MOLECULE TYPE: cDNA (ix) FEATURE:
(D) OTHER INFORMATION: from the 1st to the 69th
nucleotides of the inulinase genes (xi) SEQUENCE DESCRIPTION: SEQ ID NO: 3:

```
ATG AAG TTM GCA TAC TCC CTC TTG CTT CCA       30

TTG GCA GGA GTC AGT GCT TCA GTK ATC AAT       60

TAC AAG AGA                                   69
```

(2) INFORMATION FOR SEQ ID NO:4:

(i) SEQUENCE CHARACTERISTICS:
(A) LENGTH: 34 bases
(B) TYPE: nucleic acid
(C) STRANDEDNESS: single
(D) TOPOLOGY: linear (ii) MOLECULE TYPE: Primer DNA (xi) SEQUENCE DESCRIPTION: SEQ ID NO: 4:

```
CGCCGTCTAG ATAAAGGAT GGCAATGGTA TCAG            34
```

(2) INFORMATION FOR SEQ ID NO:5:

(i) SEQUENCE CHARACTERISTICS:
(A) LENGTH: 36 bases
(B) TYPE: nucleic acid
(C) STRANDEDNESS: single
(D) TOPOLOGY: linear (ii) MOLECULE TYPE: Primer DNA (xi) SEQUENCE DESCRIPTION: SEQ ID NO: 5:

```
TCTTCTGATC ATAGCTGTCG ACCATCAAGG GAATGT         36
```

(2) INFORMATION FOR SEQ ID NO:6:

(i) SEQUENCE CHARACTERISTICS:
(A) LENGTH: 29 bases
(B) TYPE: nucleic acid
(C) STRANDEDNESS: single
(D) TOPOLOGY: linear -continued (i i) MOLECULE TYPE: oligonucleotide DNA (x i) SEQUENCE DESCRIPTION: SEQ ID NO: 6:

GATCTATGAA GTTAGCATAC TCCCTCTTG            29

(2) INFORMATION FOR SEQ ID NO:7:

(i) SEQUENCE CHARACTERISTICS:
      (A) LENGTH: 31 bases
      (B) TYPE: nucleic acid
      (C) STRANDEDNESS: single
      (D) TOPOLOGY: linear (i i) MOLECULE TYPE: oligonucleotide DNA (x i) SEQUENCE DESCRIPTION: SEQ ID NO: 7:

TGGAAGCAAG AGGGAGTATG CTAACTTCAT A         31

(2) INFORMATION FOR SEQ ID NO:8:

(i) SEQUENCE CHARACTERISTICS:
      (A) LENGTH: 30 bases
      (B) TYPE: nucleic acid
      (C) STRANDEDNESS: single
      (D) TOPOLOGY: linear (i i) MOLECULE TYPE: oligonucleotide DNA (x i) SEQUENCE DESCRIPTION: SEQ ID NO: 8:

CTTCCATTGG CAGGAGTCAG TGCTTCAGTT           30

(2) INFORMATION FOR SEQ ID NO:9:

(i) SEQUENCE CHARACTERISTICS:
      (A) LENGTH: 30 bases
      (B) TYPE: nucleic acid
      (C) STRANDEDNESS: single
      (D) TOPOLOGY: linear (i i) MOLECULE TYPE: oligonucleotide DNA (x i) SEQUENCE DESCRIPTION: SEQ ID NO: 9:

ATTGATAACT GAAGCACTGA CTCCTGCCAA           30

(2) INFORMATION FOR SEQ ID NO:10:

(i) SEQUENCE CHARACTERISTICS:
      (A) LENGTH: 31 bases
      (B) TYPE: nucleic acid
      (C) STRANDEDNESS: single
      (D) TOPOLOGY: linear (i i) MOLECULE TYPE: oligonucleotide DNA (x i) SEQUENCE DESCRIPTION: SEQ ID NO: 10:

ATCAATTACA AGAGAATGGC AATGGTATCA G         31

(2) INFORMATION FOR SEQ ID NO:11:

(i) SEQUENCE CHARACTERISTICS:
      (A) LENGTH: 29 bases
      (B) TYPE: nucleic acid
      (C) STRANDEDNESS: single
      (D) TOPOLOGY: linear (i i) MOLECULE TYPE: oligonucleotide DNA (x i) SEQUENCE DESCRIPTION: SEQ ID NO: 11:

AATTCTGATA CCATTGCCAT TCTCTTGTA            29

( 2 ) INFORMATION FOR SEQ ID NO:12:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: oligonucleotide DNA ( x i ) SEQUENCE DESCRIPTION: SEQ ID NO: 12:

GATCTATGAA GTTCGCATAC TCCCTCTTG        29

( 2 ) INFORMATION FOR SEQ ID NO:13:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: oligonucleotide DNA ( x i ) SEQUENCE DESCRIPTION: SEQ ID NO: 13:

TGGAAGCAAG AGGGAGTATG CGAACTTCAT A        31

( 2 ) INFORMATION FOR SEQ ID NO:14:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: oligonucleotide DNA ( x i ) SEQUENCE DESCRIPTION: SEQ ID NO: 14:

CTTCCATTGG CAGGAGTCAG TGCTTCAGTG        30

( 2 ) INFORMATION FOR SEQ ID NO:15:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: oligonucleotide DNA ( x i ) SEQUENCE DESCRIPTION: SEQ ID NO: 15:

ATTGATCACT GAAGCACTGA CTCCTGCCAA        30

( 2 ) INFORMATION FOR SEQ ID NO:16:

( i ) SEQUENCE CHARACTERISTICS:
        ( A ) LENGTH: 42 bases
        ( B ) TYPE: nucleic acid
        ( C ) STRANDEDNESS: single
        ( D ) TOPOLOGY: linear ( i i ) MOLECULE TYPE: Primer DNA ( x i ) SEQUENCE DESCRIPTION: SEQ ID NO: 16:

CGCCGTCTAG ATAAAAGAAT GGCGCCTACT TCAAGTTCTA CA        42

( 2 ) INFORMATION FOR SEQ ID NO:17:

( i ) SEQUENCE CHARACTERISTICS:

(A) LENGTH: 39 bases
            (B) TYPE: nucleic acid
            (C) STRANDEDNESS: single
            (D) TOPOLOGY: linear (ii) MOLECULE TYPE: Primer DNA (xi) SEQUENCE DESCRIPTION: SEQ ID NO: 17:

TGTCGACCAT CAAGGGAATG TTTAAGTTAG TGTTGAGAT        39

(2) INFORMATION FOR SEQ ID NO:18:

(i) SEQUENCE CHARACTERISTICS:
            (A) LENGTH: 29 bases
            (B) TYPE: nucleic acid
            (C) STRANDEDNESS: single
            (D) TOPOLOGY: linear (ii) MOLECULE TYPE: oligonucleotide DNA (xi) SEQUENCE DESCRIPTION: SEQ ID NO: 18:

AATTCATGAA GTTAGCATAC TCCCTCTTG        29

(2) INFORMATION FOR SEQ ID NO:19:

(i) SEQUENCE CHARACTERISTICS:
            (A) LENGTH: 31 bases
            (B) TYPE: nucleic acid
            (C) STRANDEDNESS: single
            (D) TOPOLOGY: linear (ii) MOLECULE TYPE: oligonucleotide DNA (xi) SEQUENCE DESCRIPTION: SEQ ID NO: 19:

TGGAAGCAAG AGGGAGTATG CTAACTTCAT G        31

(2) INFORMATION FOR SEQ ID NO:20:

(i) SEQUENCE CHARACTERISTICS:
            (A) LENGTH: 16 bases
            (B) TYPE: nucleic acid
            (C) STRANDEDNESS: single
            (D) TOPOLOGY: linear (ii) MOLECULE TYPE: oligonucleotide DNA (xi) SEQUENCE DESCRIPTION: SEQ ID NO: 20:

ATCAATTACA AGAGGG        16

(2) INFORMATION FOR SEQ ID NO:21:

(i) SEQUENCE CHARACTERISTICS:
            (A) LENGTH: 12 bases
            (B) TYPE: nucleic acid
            (C) STRANDEDNESS: single
            (D) TOPOLOGY: linear (ii) MOLECULE TYPE: oligonucleotide DNA (xi) SEQUENCE DESCRIPTION: SEQ ID NO: 21:

CGCCCTCTTG TA        12

(2) INFORMATION FOR SEQ ID NO:22:

(i) SEQUENCE CHARACTERISTICS:
            (A) LENGTH: 29 bases
            (B) TYPE: nucleic acid
            (C) STRANDEDNESS: single
            (D) TOPOLOGY: linear -continued (ii) MOLECULE TYPE: oligonucleotide DNA (xi) SEQUENCE DESCRIPTION: SEQ ID NO: 22:

AATTCATGAA GTTCGCATAC TCCCTCTTG            29

(2) INFORMATION FOR SEQ ID NO:23:

(i) SEQUENCE CHARACTERISTICS:
  (A) LENGTH: 31 bases
  (B) TYPE: nucleic acid
  (C) STRANDEDNESS: single
  (D) TOPOLOGY: linear (ii) MOLECULE TYPE: oligonucleotide DNA (xi) SEQUENCE DESCRIPTION: SEQ ID NO: 23:

TGGAAGCAAG AGGGAGTATG CGAACTTCAT G            31